United States Patent [19]

Ksander

[11] Patent Number: 5,354,892

[45] Date of Patent: * Oct. 11, 1994

[54] BIARYL SUBSTITUTED 4-AMINO-BUTYRIC ACID AMIDES

[75] Inventor: Gary Ksander, Milford, N.J.

[73] Assignee: Ciba-Geigy Corporation, Ardsley, N.Y.

[*] Notice: The portion of the term of this patent subsequent to Jun. 8, 2010 has been disclaimed.

[21] Appl. No.: 8,031

[22] Filed: Jan. 25, 1993

Related U.S. Application Data

[63] Continuation of Ser. No. 824,132, Jan. 22, 1992, Pat. No. 5,217,996.

[51] Int. Cl.$^5$ ............... C07C 229/28; C07C 229/34; A61K 31/195
[52] U.S. Cl. .................... 562/444; 560/39; 560/41; 562/450
[58] Field of Search ............... 562/444, 450; 560/39, 560/41; 514/563, 533

[56] References Cited

U.S. PATENT DOCUMENTS

| | | | |
|---|---|---|---|
| 2,543,267 | 2/1951 | Bambas | 260/558 |
| 4,206,232 | 6/1980 | Ondetti et al. | 424/309 |
| 5,021,430 | 6/1991 | Ksander | 514/332 |
| 5,217,996 | 6/1993 | Ksander | 514/533 |

FOREIGN PATENT DOCUMENTS

| | | | |
|---|---|---|---|
| 0225292 | 6/1987 | European Pat. Off. | |
| 250531 | 10/1987 | Fed. Rep. of Germany | |
| 8904821 | 6/1989 | World Int. Prop. O. | 562/444 |
| 9105555 | 5/1991 | World Int. Prop. O. | |

OTHER PUBLICATIONS

Chem. Abstr. 7912p, vol. 112, No. 1, (1990).
McMurry, "Organic Chemistry", 2nd ed., Brooks/Cole Pub. Co. (1988), p. 321.

*Primary Examiner*—José G. Dees
*Assistant Examiner*—Barbara S. Frazier
*Attorney, Agent, or Firm*—Norbert Gruenfeld

[57] ABSTRACT

The invention relates to biaryl substituted 4-aminobutyric acid derivatives of formula I

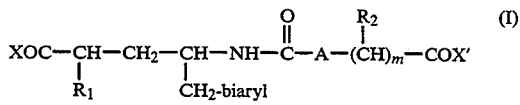

wherein COX and COX' independently represent carboxyl or carboxyl derivatized in form of a pharmaceutically acceptable ester or amide; $R_1$ represents hydrogen, lower alkyl, $C_3$-$C_7$-cycloalkyl-lower alkyl, aryl-lower alkyl, biaryl-lower alkyl, lower alkoxy, aryl-lower alkoxy, aryloxy, N-lower alkylamino, N,N-di-lower alkylamino, N-aryl-lower alkylamino, N,N-di-aryl-lower alkylamino, N-arylamino, N,N-diarylamino, lower alkanoylamino, aryl-lower alkanoylamino or aroylamino; $R_2$ represents hydrogen, hydroxy, lower alkoxy, lower alkyl, aryl-lower alkyl, $C_3$-$C_7$-cycloalkyl-lower alkyl, amino-lower alkyl, hydroxy-lower alkyl, lower alkylthio-lower alkyl, lower alkoxy-lower alkyl, aryl-lower alkylthio-lower alkyl or aryl-lower alkoxy-lower alkyl; biaryl represents phenyl substituted by carbocyclic or heterocyclic aryl; A represents a direct bond, lower alkylene, phenylene or cyclohexylene; m represents 1 or zero, provided that m represents 1 when A is a direct bond; or pharmaceutically acceptable salts thereof; pharmaceutical compositions comprising said compounds; methods for the preparation of said compounds and for the preparation of intermediates; and methods of treating disorders in mammals which are responsive to the inhibition of neutral endopeptidases by administration of said compounds to mammals in need of such treatment.

10 Claims, No Drawings

BIARYL SUBSTITUTED 4-AMINO-BUTYRIC ACID AMIDES

This is a continuation of Ser. No. 07/824,132, filed Jan. 22, 1992, now U.S. Pat. No. 5,217,996.

SUMMARY OF THE INVENTION

Endogenous atrial natriuretic peptides (ANP), also called atrial natriuretic favors (ANF) have diuretic, natriuretic and vasorelaxant functions in mammals. The natural ANF peptides are metabolically inactivated, in particular by a degrading enzyme which has been recognized to correspond to the enzyme neutral endopeptidase (NEP) EC 3.4. 24.11, also responsible for e.g. the metabolic inactivation of enkephalins.

The aim of the present invention is to provide novel biaryl substituted 4-amino-butyric acid amide derivatives described below which arc useful as neutral endopeptidase (NEP) inhibitors, e.g. as inhibitors of the ANF-degrading enzyme in mammals, so as to prolong and potentate the diuretic, natriuretic and vasodilator properties of ANF in mammals, by inhibiting the degradation thereof to less active metabolites. The compounds of the invention arc thus particularly useful for the treatment of conditions and disorders responsive to the inhibition of neutral endopeptidase EC 3.4. 24.11, particularly cardiovascular disorders, such as hypertension, renal insufficiency including edema and salt retention, pulmonary edema and congestive heart failure. By virtue of their inhibition of neutral endopeptidase, the compounds of the invention may also be useful for the treatment of pain, depression and certain psychotic conditions. Other potential indications include the treatment of angina, premenstrual syndrome, Meniere's disease, hyperaldosteronism, hypercalciuria, ascites, glaucoma, asthma, inflammations and gastrointestinal disorders such as diarrhea, irritable bowel syndrome and gastric hyperacidity.

The present invention relates to biaryl substituted 4-amino-butyric acid derivatives of formula I

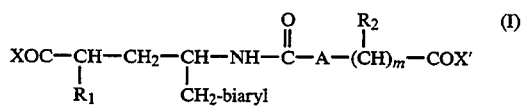

wherein COX and COX' independently represent carboxyl or carboxyl derivatized in form of a pharmaceutically acceptable ester or amide; $R_1$ represents hydrogen, lower alkyl. $C_3$—$C_7$-cycloalkyl-lower alkyl, aryl-lower alkyl, biaryl-lower -alkyl, lower alkoxy, aryl-lower alkoxy, aryloxy, N-lower alkylamino. N,N-di-lower alkylamino, N-aryl-lower alkylamino, N,N-di-aryl-lower alkylamino, N-arylamino, N,N-diarylamino, lower alkanoylamino, aryl-lower alkanoylamino or aroylamino; $R_2$ represents hydrogen, hydroxy, lower alkoxy, lower alkyl, aryl-lower alkyl, $C_3$-$C_7$-cycloalkyl-lower alkyl, amino-lower alkyl, hydroxy-lower alkyl, lower alkylthio-lower alkyl, lower alkoxy-lower alkyl, aryl-lower alkylthio-lower alkyl or aryl-lower alkoxy-lower alkyl; biaryl represents phenyl substituted by carbocyclic or heterocyclic aryl; A represents a direct bond, lower alkylene, phenylene or cyclohexylene; m represents 1 or zero, provided that m represents 1 when A is a direct bond; or a pharmaceutically acceptable salt thereof.

Pharmaceutically acceptable ester and amide derivatives are preferably prodrug derivatives, such being convertible by solvolysis or under physiological conditions to the free carboxylic acids of formula I wherein COX and/or COX' represent carboxyl.

Compounds of formula I and derivatives thereof, depending on the nature of substituents, possess one or more asymmetric carbon atoms. The resulting diastereoisomers and optical antipodes are encompassed by the instant invention.

DETAILED DESCRIPTION OF THE INVENTION

The definitions used herein, unless denoted otherwise, have the following meanings within the scope of the present invention.

The term biaryl represents phenyl substituted by carbocyclic aryl or heterocyclic aryl as defined herein, ortho, meta or para to the point of attachment of the phenyl ring, advantageously para; biaryl is also represented as the —$C_6H_4$—$R_3$ substituent in formulae herein.

Carbocyclic aryl preferably represents preferably monocyclic carbocyclic aryl or optionally substituted naphthyl.

Monocyclic carbocyclic aryl represents optionally substituted phenyl, being preferably phenyl or phenyl substituted by one to three substituents, such being advantageously lower alkyl, hydroxy, lower alkoxy, lower alkanoyloxy, halogen, cyano, trifluoromethyl, lower alkanoylamino or lower alkoxycarbonyl. Monocyclic carbocyclic aryl particularly preferably represents phenyl or phenyl substituted by lower alkyl, lower alkoxy, hydroxy, halogen, cyano or trifluoromethyl.

Optionally substituted naphthyl represents 1- or 2-naphthyl or 1- or 2-naphthyl preferably substituted by lower alkyl, lower alkoxy or halogen.

Heterocyclic aryl represents preferably monocyclic heterocyclic aryl such as optionally substituted thienyl, indolyl, imidazolyl, furanyl, pyridyl, pyrrolyl or N-lower alkylpyrrolyl.

Optionally substituted furanyl represents 2- or 3-furanyl or 2- or 3-furanyl preferably substituted by lower alkyl.

Optionally substituted pyridyl represents 2-, 3- or 4-pyridyl or 2-, 3- or 4-pyridyl preferably substituted by lower alkyl, halogen or cyano.

Optionally substituted thienyl represents 2- or 3-thienyl or 2- or 3-thienyl preferably substituted by lower alkyl.

Optionally substituted indolyl represents preferably 2- or 3-indolyl or 2- or 3-indolyl preferably substituted by lower alkyl, lower alkoxy or halogen.

Optionally substituted imidazolyl is preferably 1- or 2-imidazolyl or 1- or 2-imidazolyl preferably substituted by lower alkyl.

Aryl as in aryl-lower alkyl, aryl-lower alkoxy, aryloxy, N-arylamino, N,N-diarylamino, aryl-lower alkoxycarbonyl or aryl-lower alkanoylamino is preferably phenyl or phenyl substituted by one or two of lower alkyl, lower alkoxy, hydroxy, lower alkanoyloxy, halogen, trifluoromethyl, cyano, lower alkanoylamino or lower alkoxycarbonyl.

The term "lower" referred to herein in connection with organic radicals or compounds respectively defines such with up to and including 7, preferably up and including 4 and advantageously one or two carbon atoms. Such may be straight chain or branched.

A lower alkyl group preferably contains 1–4 carbon atoms and represents e.g. ethyl, n- or iso-propyl, n-, iso-, sec.- or tert.-butyl or advantageously methyl.

A lower alkoxy group preferably contains 1–4 carbon atoms and represents for example methoxy, n-propoxy, isopropoxy, n-, iso-, sec.- or tert.-butoxy or advantageously ethoxy.

Aryl-lower alkyl is advantageously benzyl or phenethyl optionally substituted by one or two of lower alkyl, lower alkoxy, hydroxy, lower alkanoyloxy, halogen or trifluoromethyl.

Aryl-lower alkoxy represents advantageously e.g. benzyloxy, benzyloxy substituted by lower alkyl, lower alkoxy, lower alkanoyloxy, halogen or trifluoromethyl, or pyridylmethoxy.

Aryloxy preferably represents phenoxy or phenoxy substituted by lower alkyl, lower alkoxy, lower alkanoyloxy, halogen or trifluoromethyl.

N-arylamino and N,N-diarylamino represent advantageously N-phenylamino or N,N-diphenylamino optionally substituted in the phenyl moieties or phenyl moieties by lower alkyl, lower alkoxy, hydroxy, lower alkanoyloxy, halogen or trifluoromethyl.

The term $C_3$–$C_7$-cycloalkyl represents a saturated cyclic hydrocarbon radical which contains 3 to 7 and preferably 5 to 7 ring carbons and is, most preferably, cyclopentyl or cyclohexyl.

The term cycloalkyl-lower alkyl represents preferably 1- or 2-(cyclopentyl or cyclohexyl)ethyl, 1-, 2- or 3-(cyclopentyl or cyclohexyl)propyl, or 1-, 2-, 3- or 4-(cyclopentyl or cyclohexyl)-butyl.

Amino-lower alkyl represents preferably amino-(ethyl, propyl or butyl), particularly omega-amino-(ethyl, propyl or butyl).

A N-lower alkylamino group preferably contains 1–4 carbon atoms in the lower alkyl portion and represents, for example, N-n-propyl-amino. N-iso-propylamino, N-n-butylamino, N-tert.-butylamino and advantageously N-methylamino or N-ethylamino.

A N,N-di-lower alkylamino group preferably contains 1–4 carbon atoms in each lower alkyl portion and represents, for example, N,N-dimethylamino, N-methyl-N -ethylamino and advantageously N,N-diethylamino.

Hydroxy-lower alkyl is for example 2-hydroxyethyl and preferably hydroxymethyl.

Lower alkylthio as in lower alkylthio-lower alkyl represents advantageously $C_1$–$C_4$-alkylthio and preferably methylthio or ethylthio.

Lower alkylene represents branched or straight chain alkylene of 1 to 7 carbon atoms, advantageously straight chain (or linear) alkylene, such as methylene, ethylene, propylene, butylene, pentylene or hexylene and most preferably straight chain $C_1$–$C_4$-alkylene.

Phenylene represents preferably 1,3 or 1,4-phenylene, advantageously 1,4-phenylene.

Cyclohexylene represents preferably 1,4-cyclohexylene.

Halogen (halo) preferably represents fluoro or chloro, but may also be bromo or iodo.

Lower alkanoyloxy advantageously contains 2 to 5 carbon atoms and is preferably acetoxy, pivaloyloxy or propionyloxy.

Lower alkanoylamino advantageously contains 2 to 5 carbon atoms and is preferably acetylamino or propionylamino.

A lower alkoxycarbonyl group preferably contains 1 to 4 carbon atoms in the alkoxy portion and represents, for example, methoxycarbonyl, n-propoxycarbonyl, iso-propoxycarbonyl or advantageously ethoxycarbonyl.

Aroylamino is preferably benzoylamino or benzoylamino substituted on the benzene ring by lower alkyl, lower alkoxy, halogen or trifluoromethyl.

Carboxyl esterified in form of a pharmaceutically acceptable ester, represents advantageously a prodrug ester that may be convertible by solvolysis or under physiological conditions to the free carboxylic acid, such being preferably $C_1$–$C_{20}$-alkoxycarbonyl, advantageously lower alkoxycarbonyl; (amino, acylamino, mono- or di-lower alkylamino)-lower alkoxycarbonyl; carboxy-lower alkoxycarbonyl, e.g. alpha-carboxy-lower alkoxycarbonyl; lower alkoxycarbonyl-lower alkoxycarbonyl, e.g. alpha-lower alkoxycarbonyl-lower alkoxycarbonyl; α-(di-lower alkylamino, amino, mono-lower alkylamino, morpholino, piperidino, pyrrolidino, 1-lower alkyl-piperazino)-carbonyl-lower alkoxycarbonyl; aryl-lower alkoxycarbonyl, preferably optionally (halo, lower alkyl or lower alkoxy)-substituted benzyloxycarbonyl, or pyridylmethoxycarbonyl; 1-(hydroxy, lower alkanoyloxy or lower alkoxy)-lower alkoxycarbonyl, e.g. pivaloyloxymethoxycarbonyl; (hydroxy, lower alkanoyloxy or lower alkoxy)-lower alkoxymethoxycarbonyl; bicycloalkoxycarbonyl-lower alkoxycarbonyl, e.g. bicyclo[2,2,1]-heptyloxycarbonyl-lower alkoxycarbonyl, especially bicyclo-[2,2,1]-heptyloxycarbonylmethoxycarbonyl such as bornyloxycarbonylmethoxycarbonyl; 1-(lower alkoxycarbonyloxy)-lower alkoxycarbonyl; 5-indanyloxycarbonyl; 3-phthalidoxycarbonyl and (lower alkyl, lower alkoxy or halo)-substituted 3-phthalidoxycarbonyl; polyhydroxy-lower alkoxycarbonyl or protected polyhydroxy-lower alkoxycarbonyl in which polyhydroxy-lower alkoxy and protected polyhydroxy-lower alkoxy represent preferably dihydroxypropyloxy or trihydroxybutyloxy wherein hydroxy groups are free or one or more, as appropriate, are protected in form of esters, e.g. a lower alkanoyl or a benzoyl ester, in form of ethers, e.g. a lower alkyl or benzyl ether, or, in case two vicinal hydroxy groups are involved, in the form of acetals or ketals, e.g. a lower alkylidene, a benzylidene or a 5- or 6-membered cycloalkylidene derivative.

Protected polyhydroxy-lower alkoxycarbonyl advantageously represents (2,2-dimethyl-1,3-dioxolan-4-yl)-methoxycarbonyl.

Acyl as in acyloxy or acylamino represents preferably lower alkanoyl, carbocyclic aryl-lower alkanoyl, aroyl, lower alkoxycarbonyl or aryl-lower alkoxycarbonyl, advantageously lower alkanoyl. Lower alkoxycarbonyl for acyl is preferably t-butoxycarbonyl (abbreviated t-BOC). Aryl-lower alkoxycarbonyl for acyl is preferably benzyloxycarbonyl (abbreviated CBZ).

Carboxy-lower alkoxycarbonyl represents advantageously e.g. 1-carboxyethoxycarbonyl.

Lower alkoxycarbonyl-lower alkoxycarbonyl represents advantageously e.g. 1-(ethoxycarbonyl)ethoxycarbonyl.

Amino-lower alkoxycarbonyl, mono-lower alkylamino-lower alkoxycarbonyl, di-(lower)alkylamino-lower alkoxycarbonyl advantageously represent e.g. aminoethoxycarbonyl, ethylaminoethoxycarbonyl, diethylaminoethoxycarbonyl.

Lower alkylidene is preferably isopropylidene.

Cycloalkylidene is preferably cyclohexylidene.

Carboxyl esterified in form of a pharmaceutically acceptable prodrug ester represents most advantageously C₁–C₄-alkoxycarbonyl, phenyloxycarbonyl, benzyloxycarbonyl optionally substituted on phenyl by lower alkyl, lower alkoxy, halo or trifluoromethyl, pivaloyloxymethoxycarbonyl, 1-(C₂–C₄-alkanoyloxy)-ethoxycarbonyl, (2,2-dimethyl-1,3-dioxolan-4-yl)-methoxycarbonyl, 5-indanyloxycarbonyl, 3-phthalidoxycarbonyl, bornyloxycarbonylmethoxycarbonyl, 1-(C₁–C₄-alkoxycarbonyloxy)-ethoxycarbonyl or 3-pyridylmethoxycarbonyl.

Carboxyl derivatized in the form of a pharmaceutically acceptable amide represents preferably carbamoyl or N-substituted carbamoyl, advantageously [lower alkylamino, arylamino, di-lower alkylamino, morpholino, N-lower alkylpiperazino, pyrrolidino, piperidino, perhydroazepino, (amino or acylamino)-lower alkylamino or aryl-lower alkylamino]-carbonyl.

Pharmaceutically acceptable salts are either pharmaceutically acceptable acid addition salts for any basic compounds of the invention or salts derived from pharmaceutically acceptable bases for any acidic compounds of the invention.

Pharmaceutically acceptable salts of basic compounds of the invention are acid addition salts, which are preferably such of therapeutically acceptable inorganic or organic acids, such as strong mineral acids, for example hydrohalic, e.g. hydrochloric or hydro-bromic acid, sulfuric, phosphoric or nitric acid; aliphatic or aromatic carboxylic or sulfonic acids, e.g. formic, acetic, propionic, succinic, glycollic, lactic, malic, tartaric, gluconic, citric, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, 1,2-ethanedisulfonic acid, benzenesulfonic, p-toluenesulfonic, naphthalenesulfonic, sulfanilic, cyclohexylsulfamic acid, or ascorbic acid.

Pharmaceutically acceptable salts of the acidic compounds of the invention, e.g. those having a free carboxyl group are salts formed with pharmaceutically acceptable bases, e.g. alkali metal salts (e.g. sodium, potassium salts), alkaline earth metal salts (e.g. magnesium, calcium salts), ammonium salts, mono-, di- or tri-lower (alkyl or hydroxyalkyl)-ammonium salts (e.g. ethanolammonium, diethanolammonium, triethanolammonium, tromethamine salts).

The compounds of the invention, of formula I and derivatives thereof may contain several asymmetric carbon atoms, depending on the nature of the substituents. Thus the compounds of the invention exist in the form of geometric isomers, racemates, diastereoisomers, pure enantiomers or mixtures thereof, all of which are within the scope of the invention.

For example, the compounds of formula I exist in isomeric forms, e.g. wherein the asymmetric carbon atom on the butyryl chain bearing the R$_l$ and/or biarylmethyl groups may either exist in the S or R configuration. The compounds of the invention, e.g. those of formula I having said two asymmetric centers exist as two different racemic diastereoisomeric forms which may be called erythro and threo depending on the relative orientation of the R$_l$ and biarylmethyl substituents of the chain. Each of the two racemates consists of the optically active enantiomers (or antipodes) having (S,S), (R,R), (R,S) or (S,R) configurations, respectively.

Preferred is the threo racemic form and particularly the enantiomeric form depicted in formula I'

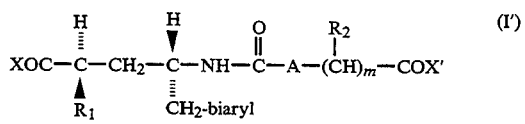

wherein COX, COX', R$_l$, R$_2$, A, biaryl and m have the meanings as defined herein above for compounds of formula I. The compounds of formulae Ia, Ib, Dc, Id, Ie and If given below are present as well, preferably in the enantiomeric form depicted in formula I'.

Illustrative thereof, in the above compounds of formula I wherein R$_1$ is lower alkyl, the carbon atom carrying said substituent is assigned the (R)-configuration; and the carbon atom carrying the biarylmethyl substituent is assigned the (S)-configuration.

More particularly, the present invention is concerned with and has for its object the compounds of formula Ia

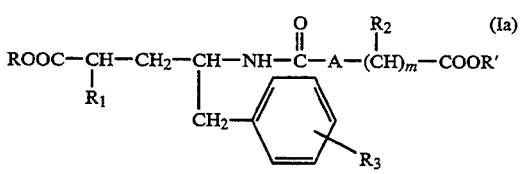

wherein COOR and COOR' independently represent carboxyl or carboxyl derivatized in form of a pharmaceutically acceptable ester, R$_1$ represents hydrogen, lower alkyl, lower alkoxy, N-lower alkylamino, lower alkanoylamino, aryl-lower alkyl, aryl-lower alkoxy, aryloxy, N-arylamino or aroylamino wherein aryl in each case represents phenyl optionally substituted by lower alkyl, lower alkoxy, halogen, hydroxy, cyano, acyloxy or trifluoromethyl, or aryl represents thienyl or furanyl optionally substituted by lower alkyl; R$_2$ represents hydrogen, hydroxy, lower alkyl or aryl-lower alkyl wherein aryl independently has the meaning given above under R$_1$; R$_3$ represents phenyl, or phenyl substituted by lower alkyl, lower alkoxy, halogen, cyano, acyloxy or trifluoromethyl; or R$_3$ represents thienyl or furanyl optionally substituted by lower alkyl; A represents a direct bond, lower alkylene, 1,4-phenylene or 1,4-cyclohexylene; m represents 1 or zero provided that m represents 1 when A is a direct bond; or a pharmaceutically acceptable salt thereof.

Advantageously, R$_3$ is located in the para position.

Particularly preferred embodiments of the invention as described above relate to:

a) compounds wherein R$_3$ is phenyl or phenyl substituted by lower alkyl, lower alkoxy, halogen, cyano, acyloxy or trifluoromethyl;

b) compounds wherein A is lower alkylene, m represents I or zero, and R$_2$ represents hydrogen, lower alkyl, hydroxy or lower alkoxy.

c) compounds wherein R$_1$ represents hydrogen, lower alkyl, lower alkoxy or aryl-lower alkyl wherein aryl represents phenyl optionally substituted by one or two of lower alkyl, lower alkoxy, halogen, hydroxy, cyano, acyloxy or trifluoromethyl; most preferably compounds wherein R$_1$ represents lower alkoxy or lower alkyl.

A particular embodiment of the invention relates to compounds of formula Ib

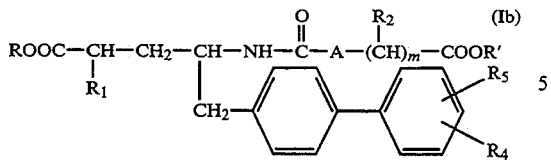

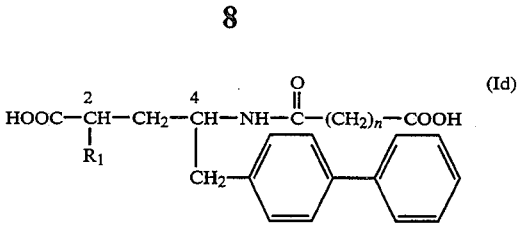

wherein COOR and COOR' independently represent carboxyl or carboxyl derivatized in form of a pharmaceutically acceptable ester, $R_1$ is hydrogen, lower alkyl, lower alkoxy or aryl-lower alkyl wherein aryl represents phenyl optionally substituted by lower alkyl, lower alkoxy, halogen, hydroxy, cyano, acyloxy or trifluoromethyl; $R_2$ represents hydrogen, hydroxy or lower alkyl; $R_4$ and $R_5$ independently represent hydrogen, lower alkyl, hydroxy, lower alkoxy, halogen, cyano or trifluoromethyl; A represents lower alkylene; m represents 1 or zero; or a pharmaceutical acceptable salt thereof.

Particularly preferred are compounds of formula Ic

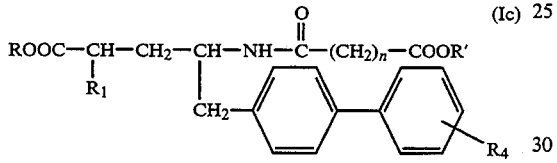

wherein COOR and COOR' independently represent carboxyl or carboxyl derivatized in form of a pharmaceutically acceptable ester, $R_1$ is lower alkyl or lower alkoxy; $R_4$ represents hydrogen, lower alkyl, lower alkoxy, halogen, or trifluoromethyl; n represents an integer 1 through 6; or a pharmaceutical acceptable salt thereof.

Preferred are compounds of formula Ic wherein COOR and COOR' independently represent carboxyl, $C_1$–$C_{20}$-alkoxycarbonyl, (carbocyclic or heterocyclic aryl)-lower alkoxycarbonyl, (di-lower alkylamino, N-lower alkylpiperazino, morpholino, pyrrolidino, piperidino or perhydrazepino)-$C_2$ to $C_4$-alkoxycarbonyl, dihydroxypropyloxycarbonyl protected in form of a ketal, 5-indanyloxycarbonyl, 3-phthalidoxycarbonyl, Bicycloalkoxycarbonyl-lower alkoxycarbonyl, α-(lower alkoxycarbonyl or di-lower alkylaminocarbonyl)-lower alkoxycarbonyl, 1-(lower alkoxycarbonyloxy)-lower alkoxycarbonyl or 1-(lower alkanoyloxy)-lower alkoxycarbonyl; or a pharmaceutically acceptable salt thereof.

Particularly preferred are said compounds of formula Ic wherein COOR and COOR' independently represent carboxyl, $C_1$–$C_4$-alkoxycarbonyl, 3-pyridylmethoxycarbonyl, benzyloxycarbonyl optionally substituted on phenyl by lower alkyl, lower alkoxy, halo or trifluoromethyl, 5-indanyloxycarbonyl, 1-($C_2$–$C_5$-alkanoyloxy)-ethoxycarbonyl, 3-phthalidoxycarbonyl, (2,2'-dimethyl-1,3-dioxolan-4-yl)-methoxycarbonyl, bornyloxycarbonylmethoxycarbonyl, 1-($C_1$–$C_4$-alkoxycarbonyloxy)-ethoxycarbonyl; or a pharmaceutically acceptable salt thereof.

A preferred embodiment of the invention relates to compounds of formula Id wherein $R_1$ is lower alkyl; n is an integer 1 through 4; or a pharmaceutically acceptable mono- or di-ester derivative thereof in which one or two of the acidic hydroxy groups of the carboxyl functional groups are esterified in form of a mono- or di-pharmaceutically acceptable ester, or a pharmaceutically acceptable salt thereof; or an optical antipode thereof.

Preferred are said compounds of formula Id wherein $R_1$ is methyl and n is 2; and mono- or di-esters thereof.

As discussed before, the butyric acid compounds of e.g. formula Id exist in two distinct diastereomeric forms which may be called erythro and threo. Preferred are e.g. the compounds of formula Id as the threo diastereomer (racemate), more particularly as the enantiomeric form having the R-configuration at C-atom 2 and the S-configuration at C-atom 4 and wherein the butyryl portion is as depicted in formula Id'

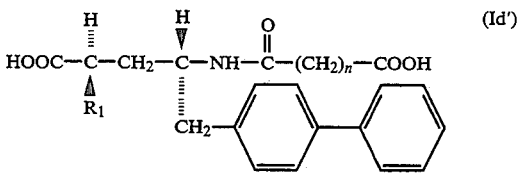

wherein $R_1$ and n are as defined under formula Id; or a pharmaceutical acceptable mono- or diester derivative thereof; or a pharmaceutically acceptable salt thereof.

Particularly preferred are compounds of formula Ie

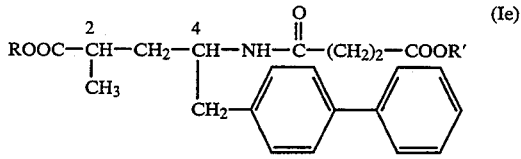

wherein COOR and COOR' independently represent carboxyl or carboxyl esterified in form of a pharmaceutical acceptable prodrug ester, or a pharmaceutically acceptable salt thereof.

Particularly preferred embodiments of the invention as described above relate to:

(a) compounds of the above formula Ie wherein R and R' independently represent hydrogen, $C_1$–$C_4$-alkyl, benzyl optionally substituted on phenyl by lower alkyl, lower alkoxy, halo or trifluoromethyl, pivaloyloxymethyl, 1-($C_2$–$C_4$-alkanoyloxy)-ethyl, (2,2-dimethyl-1,3-dioxolan4-yl)-methyl, 5-indanyl, 3-phthalidyl, bornyloxycarbonylmethyl, 1-($C_1$–$C_4$-alkoxycasbonyloxy)-ethyl or 3-pyridylmethyl; or a pharmaceutically acceptable salt thereof;

(b) compounds of the above formula Ie wherein COOR' is carboxyl; and COOR represents carboxyl or carboxyl derivatized in form of a pharmaceutically acceptable ester; or a pharmaceutically acceptable salt thereof;

(c) compounds of the above formula Ie having the R-configuration at C-atom 2 and the S-configuration at C-atom 4;

(d) the compound according to the above formula Ie wherein COOR is ethoxycarbonyl and COOR' is carboxyl, namely being 4-[N-(3-carboxy-1-oxopropyl)amino]-4-(p-phenylphenylmethyl)-2-methylbutanoic acid ethyl ester, the (2R, 4S)antipode thereof or a pharmaceutical acceptable salt thereof.

The novel compounds of the invention are pharmacologically potent neutral endopeptidase enzyme inhibitors which inhibit e.g. the degradation of atrial natriuretic factors (ANF) in mammals. They thus potentiate the diuretic and natriuretic effect of exogenous or endogenous ANF in mammals.

The compounds of the invention are thus particularly useful in mammals as diuretic, natriuretic (saluretic) and antihypertensive agents for the treatment of e.g. hypertension, congestive heart failure and edema.

As neutral endopeptidase inhibitors, the compounds are also e.g. enkephalinase inhibitors so as to inhibit the degradation of endogenous enkephalins and may thus also be useful for the treatment of pain in mammals.

The above-cited properties are demonstrable in vitro and in vivo tests, using advantageously mammals, e.g. mice, rats, dogs, monkeys or isolated organs, tissues and preparations thereof. Said compounds can be applied in vitro in the form of solutions, e.g. preferably aqueous solutions, and in vivo either enterally, parenterally, advantageously intravenously, e.g. as a suspension or in aqueous solution. The dosage in vitro may range between about $10^{-4}$ molar and $10^{-9}$ molar concentrations. The dosage in vivo may range depending on the route of administration, between about 0.01 and 50 mg/kg, advantageously between about 1.0 and 25 mg/kg.

The analgesic activity can be determined by measuring the potentiation of the analgesic effects of enkephalin and derivatives thereof, and by classical analgesic tests, such as the phenyl-p-benzoquinone induced writing test [J. Pharmacol. Exp. Therap. 125, 237 (1959)] and the hot plate test in the mouse [J. Pharmacol. Exp. Therap. 107,385 (1953).

The antihypertensive activity can be determined in the spontaneously hypertensive rat, Goldblatt rat or Goldblatt dog by direct measurement of blood pressure. Advantageously, the effect is measured in the DOCA-salt hypertensive rat and/or renal hypertensive rat or dog model.

The diuretic (saluretic) activity can be determined in standard diuretic screens, e.g. as described in "New Antihypertensive Drugs", Spectrum Publications, 1976, pages 307–321, or by measuring the potentiation of atrial natriuretic factor-induced natriuresis and diuresis in the rat.

The potentiation of ANF can also be determined by measuring the increase in ANF plasma level achieved.

The in vitro inhibition of neutral endopeptidase (NEP) 3.4.24.11 can be determined as follows:

Neutral endopeptidase 3.4.24.11 activity is determined by the hydrolysis of the substrate glutaryl-Ala-Ala-Phe-2-naphthylamide (GAAP) using a modified procedure of Orlowski and Wilk (1981). The incubation mixture (total volume 125 $\mu$l) contains 4.2 $\mu$g of protein (rat kidney cortex membranes prepared by method of Maeda ct al, 1983), 50 mM tris buffer, pH 7.4 at 25° C., 500 $\mu$M substrate (final concentration), and leucine aminopeptidase M (2.5 $\mu$g). The mixture is incubated for 10 minutes at 25° C. and 100 $\mu$l of fast garnet (250 $\mu$g fast garnet/ml of 10% Tween 20 in 1M sodium acetate, pH 4.2) is added. Enzyme activity is measured spectrophotometrically at 540 nm. One unit of NEP 24.11 activity is defined as 1 nmol of 2-naphthylamine released per minute at 25° C. at pH 7.4. $IC_{50}$ values are determined, i.e. the concentration of test compound required for 50% inhibition of the release of 2-naphthylamine.

Neutral endopeptidase activity is also determined using ANF as a substrate. Atrial natriuretic factor degrading activity is determined by measuring the disappearance of rat-ANF (r-ANF) using a 3 minute reverse phase-HPLC separation. An aliquot of the enzyme in 50 mM Tris HCl buffer, pH 7.4, is preincubated at 37° C. for 2 minutes and the reaction is initiated by the addition of 4 nmol of r-ANF in a total volume of 50 $\mu$l. The reaction is terminated after 4 minutes with the addition of 30 $\mu$l of 0.27% trifluoroacetic acid (TFA). Forty microliters of the mixture is injected into a reverse phase-HPLC and analyzed using a C4 cartridge in a 3 minute, isocratic separation. Twenty-three percent of buffer B (0.1% TFA in 80% acetonitrile) is used. Buffer A is 0.1% TFA in water. One unit of activity is defined as the hydrolysis of 1 nmol of r-ANF per minute at 37° C. at pH 7.4. $IC_{50}$ values are determined, i.e. the concentration of test compound required for 50% inhibition of the hydrolysis of ANF.

The test compound is dissolved in dimethyl sulfoxide or 0.25M sodium bicarbonate solution, and the solution is diluted with pH 7.4 buffer to the desired concentration.

In vitro testing is most appropriate for the free carboxylic acids of the invention.

The effect of the compounds of the invention on rat plasma ANF concentration can be determined as follows:

Male Sprague-Dawley rats (275–390 g) are anesthetized -with ketamine (150 mg/kg)/acepromazine (10%) and instrumented with catheters in the femoral artery and vein to obtain blood samples and infuse ANF. respectively. The rats are tethered with a swivel system and are allowed to recover for 24 hours before being studied in the conscious, unrestrained state.

In this assay, plasma ANF levels are determined in the presence and absence of NEP inhibition. On the day of study, all rats are infused continuously with ANF at 450 ng/kg/min. i.v. for the entire 5 hours of the experiment. Sixty minutes after beginning the infusion, blood samples for baseline ANF measurements are obtained (time 0) and the rats are then randomly divided into groups treated with the test compound or vehicle. Additional blood samples are taken 30, 60, 120, 180 and 240 minutes after administration of the test compound.

Plasma concentrations are determined by a specific radioimmunoassay. The plasma is diluted (X 12.5, X 25 and X 50) in buffer containing: 50 mM Tris (pH 6.8), 154 mM NaCl, 0.3% bovine serum albumin, 0.01% EDTA. One hundred microliters of standards [rANF (99–126)] or samples are added to 100 $\mu$l of rabbit anti-rANF serum and incubated at 4° C. for 16 hours. Ten thousand cpm of [$^{125}$I]rANF are then added to the reaction mixture which is incubated at 4° C. for an additional 24 hours. Goat anti-rabbit IgG serum coupled to paramagnetic particles is added to the reaction mixture and bound [$^{125}$I]rANF is pelleted by exposing the mixture to an attracting magnetic rack. The supernatant is decanted and the pellets counted in a gamma counter. All determinations are performed in duplicate. Plasma ANF levels are expressed as a percent of those measured in vehicle-treated animals which received ANF alone (450 ng/kg/min i.v.).

Illustrative of the invention, N-(3-carboxy-1-oxopropyl)-(4S)-(p-phenylphenylmethyl)-4-amino-2R-methylbutanoic acid ethyl ester at doses of about 1–30 mg/kg p.o., administered in 10% ethanol/polyethylene glycol (PEG) 400, produces significant increases in plasma ANF levels.

The antihypertensive effect can be determined in desoxycorticosterone acetate (DOCA)-salt hypertensive rats.

DOCA-salt hypertensive rats (280–380 g) are prepared by the standard method. Rats underwent a unilateral nephrectomy and one week later are implanted with silastic pellets containing 100 mg/kg of DOCA. The rats are maintained on 1% NaCl/0.2% KCl drinking water for three to five weeks until sustained hypertension is established. The antihypertensive activity is evaluated at this time.

Two days before an experiment, the rats are anesthetized with methoxyflurane and instrumented with catheters in the femoral artery to measure arterial blood pressure. Forty-eight hours later, baseline arterial pressure and heart rate are recorded during a 1 hour period. The test compound (30 mg/kg p.o.) or vehicle is then administered and the same cardiovascular parameters are monitored for an additional 5 hours.

Illustrative of the invention, N-(3-carboxy-1-oxopropyl)-(4S)-(p-phenylphenylmethyl)4-amino-2R-methylbutanoic acid ethyl ester at a dose of 30 mg/kg p.o., administered in PEG 400, produces a significant reduction in blood pressure in the DOCA-salt hypertensive rat model.

The potentiation of the natriuretic effect of ANF can be determined as follows:

Male Sprague-Dawley rats (280–360 g) are anesthetized with Inactin (100 mg/kg i.p.) and instrumented with catheters in the femoral artery, femoral vein and urinary bladder to measure arterial pressure, administer ANF and collect urine, respectively. A continuous infusion of normal saline (33 $\mu$l/min) is maintained throughout the experiment to promote diuresis and sodium excretion. The experimental protocol consists of an initial 15 minute collection period (designated as pre-control) followed by three additional collection periods. Immediately after completion of the pre-control period, test compound or vehicle is administered; nothing is done for the next 45 minutes. Then, blood pressure and renal measurements are obtained during a second collection period (designated control; 15 min). At the conclusion of this period, ANF is administered (1 $\mu$g/kg i.v. bolus) to all animals and arterial pressure and renal parameters are determined during two consecutive 15 minutes collection periods.

Mean arterial pressure, urine flow and urinary sodium excretion are determined for all collection periods. Blood pressure is measured with a Gould p50 pressure transducer, urine flow is determined gravimetrically, sodium concentration is measured by flame photometry, and urinary sodium excretion is calculated as the product of urine flow and urine sodium concentration.

The compounds of the invention are thus particularly useful as inhibitors of neutral endopeptidase, enhancing the potency and duration of action of atrial natriuretic peptide(s). The compounds are therefore particularly useful for the treatment of cardiovascular disorders such as hypertension, edema and salt retention, and cardiac conditions such as congestive heart failure.

The compounds of the invention of formula I may be prepared using the following process which comprises: condensing a compound of formula II

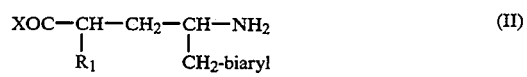

wherein COX, $R_1$ and biaryl have the meaning as defined above, in temporarily protected form if required; with a compound of formula III

or a reactive functional derivative thereof, wherein A, $R_2$, m and COX' have the meaning as defined above, in temporarily protected form if required; and, if temporarily protecting any interfering reactive group(s), removing said protecting group(s), and then isolating the resulting inventive compound; and, if desired, converting any resulting compound into another compound of the invention, and/or, if desired, converting a resulting free compound into a salt or a resulting salt into the free compound or into another salt, and/or, if desired, separating a mixture of isomers or racemates obtained into the single isomers or racemates, and/or, id desired, resolving a racemate obtained into the optical antipodes.

In starting compounds and intermediates which are convened to the compounds of the invention in a manner described herein, functional groups present, such as carboxyl, amino and hydroxy groups, are optionally protected by conventional protecting groups that are common in preparative organic chemistry. Protected carboxyl, amino and hydroxy groups are those that can be convened under mild conditions into free carboxyl, amino and hydroxy groups without other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (carboxyl group, amino group etc.), the structure and stability of the molecule of which the substituent is a pan, and the reaction conditions.

Well-known protecting groups that meet these conditions and their introduction and removal are described, for example, in J. F. W. McOmie, "Protective Groups in Organic Chemistry", Plenum Press, London, New York 1973, T. W. Greene, "Protective Groups in Organic Synthesis", Wiley, New York 1984, and also in "The Peptides", Vol. I, Schroeder and Luebke, Academic Press, London, New York, 1965.

The preparation of compounds of the invention according to the above process, i.e. the condensation of an amine of formula II with the acid of formula III, or a functional reactive derivative thereof, is carried out by methodology well-known for peptide synthesis.

Reactive functional derivatives of compounds of formula III are preferably halides, anhydrides such as succinic anhydride, glutaric anhydride, or mixed anhydrides such as the pivaloyl, alkoxycarbonyl or cyanoacetyl anhydride.

The condensation of an amine of formula II with a free carboxylic acid of formula III is carried out advantageously in the presence of a condensing agent such as dicyclohexylcarbodiimide or N-(3-dimethylaminopropyl)-N'-ethylcarbodiimide and hydroxybenzotriazole in an inert polar solvent such as dimethylformamide or methylene chloride, preferably at room temperature.

The condensation of an amine of formula II with a reactive functional derivative of an acid of formula III in the form of an acid halide, advantageously an acid chloride, anhydride or mixed anhydride, is carried out in an inert solvent such as toluene or methylene chloride, advantageously in the presence of a base, e.g. an inorganic base such as potassium carbonate or an organic base such as triethylamine or pyridine, preferably at room temperature.

The starting materials of formula III are acids or functional derivatives thereof known in the art or which may be prepared by conventional methods known in the art.

The starting materials of formula II are known or, if new, may be prepared according to conventional methods, e.g., those illustrated by the examples herein.

For example, the compounds of formula II may be prepared by converting a compound of formula IV

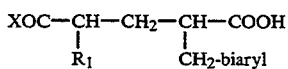

(IV)

wherein COX, $R_1$ and biaryl have the meaning mentioned above, in temporarily protected form if required, into a suitable carboxylic acid amide or carboxylic acid azide and then subjecting this compound to a Hofmann reaction or to a Curtius rearrangement in a manner well known in the art. The compounds of formula IV are known, for example, from U.S. Pat. No. 5,021,430 or may be prepared analogous to the methods described therein.

In a preferred alternative route, the starting materials of formula II may be prepared by (a) reducing the carboxylic group of a biarylalanine of formula V

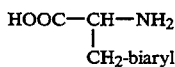

(V)

in temporarily protected form if required, to yield the respective aldehyde;

(b) subsequently reacting said aldehyde with a triphenylphosphonium compound of formula VI

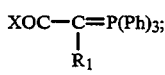

(VI)

(c) hydrogenating the resulting compound of formula VII

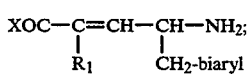

(VII)

and, if temporarily protecting any interfering reactive group(s), removing said protective group(s) and then isolating the resulting product. In the above formulae V, VI and VII, the variables COX, $R_1$ and biaryl have the meaning as defined under formula I. The above reaction steps (a), (b) and (c) are carried out by methodology well-known in the an.

For example, in step (a) the compound of formula V, advantageously an amino protected compound of formula V, is reacted first of all with a hydroxylamine or a salt thereof, e.g. with N,O-dimethylhydroxylamine hydrochloride; the resulting hydroxylmine amide is then reduced to the aldehyde in a conventionel manner, e.g. with lithium aluminum hydride.

Reaction step (b) represents a conventional Wittig reaction which may be performed in a manner known in the art.

Reaction step (c) as well represents a commonly known hydrogenation reaction which may be performed e.g. with molecular hydrogen in the presence of a suitable, catalyst such as palladium/charcoal.

Biarylalanines of formula V are either known in the art or can be prepared according to methods reported in the art.

As to the preparation of the biarylalanines of formula V as starting materials in optically active form, such can be prepared e.g. by resolution or by one of the following methods:

(a) Adapting a method described in Tetrahedron Letters 1988, 6075, a biarylmethanol, e.g. 4-biphenylylmethanol, is convened to a reactive derivative, e.g. the bromide, which is then condensed with an N-acyl derivative of 2,3-diphenyl-6-oxomorpholine, e.g. the N-carbobenzyloxy-(2R,3S)-isomer, in the presence of a strong base such as sodium bis-trimethylsilylamide, to yield e.g. N-carbobenzyloxy-2(R), 3(S), 5(S)-6-oxo-2,3-diphenyl-5-(4-biphenylylmethyl)morpholine. Catalytic hydrogenolysis, e.g. using hydrogen and palladium on charcoal as catalyst, yields the optically active (S)-(+)-4-biphenylalanine.

(b) Alternatively, using the Pd (0)-catalyzed cross-coupling reaction described in Tetrahedron Letters 31, 1665 (1990), J. Organic Chemistry 55, 906 (1990) and Tetrahedron 45, 6670 (1989) as developed by W. Shieh et al, the substantially optically pure chiral biarylalanines, of the formula

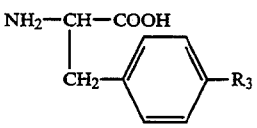

or the N-acyl and/or carboxy ester derivatives thereof wherein $R_3$ has meaning as defined hereinabove, can be prepared by: condensing a reactive esterified optically active tyrosine derivative of the formula

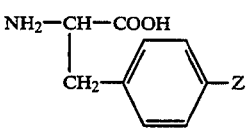

wherein the amino and carboxy groups are in protected form (as N-acyl and esterified carboxy ester derivatives), and Z represents reactive esterified hydroxy (advantageously trifluoromethylsulfonyloxy) with an aryl boronic acid in which aryl corresponds to $R_3$ as defined above, in the presence of a palladium (0) catalyst, in particular tetrakis(triphenylphosphine)palladium (0), and in the presence of an anhydrous base (such as an alkali metal carbonate), in an inert solvent (such as xylene or toluene) at an elevated temperature ranging from about 50° to 150° C., and removing any protecting groups as required.

For example, N-t-butoxycasbonyl-tyrosine methyl ester is first converted to N-t-butoxycarbonyl-4-trifluoromethylsulfonyloxy-phenylalanine methyl ester (N-t-butoxycarbonyltyrosine triflate methyl ester). This compound is then condensed with an arylboronic acid (e.g. phenylboronic acid) in the presence of anhydrous potassium carbonate, and tetrakis (triphenylphosphine) palladium (0) complex as catalyst, in toluene preferably at an elevated temperature, advantageously at about 100° to obtain N-t-butoxycarbonyl-4-biphenylalanine methyl ester. After N-deacylation, substantially optically pure 4-biphenylalanine methyl ester is obtained with a configuration corresponding to that of the tyrosine derivative used as starting material.

The arylboronic acids are either commercial or can be prepared as described in the literature, e.g. J. Org. Chem. 49, 5237 (1984).

The triphenylphosphonium compounds of formula VI are either known in the art or can be prepared according to methods reported in the art.

Compounds of the invention wherein COX or COX' represent carboxyl derivatized in form of a pharmaceutically acceptable amide can also be prepared according to the above methods using corresponding starting materials wherein COX or COX' represent carbamoyl or N-substituted carbamoyl.

The compounds of the invention so obtained, can be convened into each other according to conventional methods. Thus, for example, resulting amides or esters may be hydrolyzed with aqueous alkalies, such as alkali metal carbonates or hydroxides. Resulting free acids may be esterified with e.g. said unsubstituted or substituted alkanols or reactive esterified derivatives thereof such as alkyl halides, or diazoalkanes. Free acids are also converted into said metal, ammonium or acid addition salts in conventional manner.

Thus, any resulting free acid or base can be converted into a corresponding metal, ammonium or acid addition salt respectively, by reacting it with an equivalent amount of the corresponding base, basic salt, acid or ion exchange preparation, e.g. said free acids with alkali or ammonium hydroxides or carbonates, or e.g. free amines with said inorganic or organic acids respectively. Any resulting salt may also be converted into the free compound, by liberating the latter with stronger acids or bases, respectively. In view of the close relationship between the free compounds and the salts thereof, whenever a compound of the invention, or intermediate, is referred to in this context, a corresponding salt is also intended, provided such is possible or appropriate under the circumstances.

The compounds, including their salts, may also be obtained in the form of their hydrates, or include other solvents used for the crystallization. Furthermore, the functional derivatives of the free acids of formula I, wherein the carboxy groups are esterified by identical or different radicals may be prepared by condensing a free acid of formula I or a mono- or all-ester derivative thereof with an esterifying agent of the formula VIII $$R_6\text{—}Z \qquad \text{(VIII)}$$

wherein Z represents hydroxy or a reactive esterified hydroxyl group; and $R_6$ represents an esterifying radical as defined herein for the carboxylic esters (encompassed e.g. by COX or COX' representing esterified carboxy), in particular said non-aromatic radicals.

A reactive esterified hydroxyl group, such as Z in a compound of the formula VIII, is a hydroxyl group esterified by a strong inorganic or organic acid. Corresponding Z groups are in particular halo, for example chloro, bromo or preferably iodo, also sulfonyloxy groups, such as lower alkyl- or arylsulfonyloxy groups, for example (methane-, ethane-, benzene- or toluene-) sulfonyloxy groups, also the trifluoromethylsulfonyloxy group.

The esterification of the carboxyl groups, optionally in salt form, with a compound of formula VIII wherein Z represents a reactive esterified hydroxyl group, is performed in a manner known per se, in the presence of for example an organic base, such as an organic amine, for example a tertiary amine, such as tri-lower alkylamine, for example trimethylamine, triethylamine or ethyl-di-isopropylamine, an N,N-di-lower-alkyl-aniline, for example N,N-di-methylaniline, a cyclic tertiary amine, such as an N-lower-alkylated morpholine, for example N-methyl-morpholine, a base of the pyridine type, for example pyridine, an inorganic base, for example hydroxides, carbonates, or hydrogen carbonates of alkali metals or alkaline-earth metals, for example sodium, potassium or calcium hydroxide, carbonate or hydrogen carbonate, or a quaternary ammonium base, such as a tetraalkylammonium hydroxide, carbonate or hydrogen carbonate, for example in which alkyl is e.g. methyl, ethyl, propyl, isopropyl, butyl, or the like, or an alkali metal salt of bis-trialkylsilylamide (e.g. trimethyl) optionally in the presence of a crown ether such as 18-crown-6 in a suitable inert solvent or solvent mixture, e.g. acetonitrile, toluene, and the like.

A trifunctional free acid, e.g. of the formula I, or a monoester or diester thereof, is preferably first convened into a salt of one of the stated organic or inorganic bases, especially into the sodium or potassium salt, and is then reacted with a compound of the formula VIII. The compounds of formula VIII are known or can be prepared by methods well-known to the art.

A compound of the formula or VIII wherein Z is a reactive esterified hydroxyl group can be prepared in situ. For example, a compound of the formula VIII wherein Z is chloro can be convened by treatment with sodium iodide in a solvent, for example in acetone or acetonitrile, into a compound of the formula VIII wherein Z is iodo; or esterification can be carded out with a chloro compound of the formula VIII in the presence of sodium iodide.

Esterification of a compound with a free carboxyl group using in excess an alcohol of formula VIII (wherein Z represents hydroxy) is carried out in a manner known per se, e.g. in the presence of an acid catalyst e.g. sulfuric acid or boron trifluoride etherate, preferably at an elevated temperature, advantageously ranging from about 40° C. to 100° C. Alternately, the esterification of a compound with a free carboxyl group can be carried out with at least an equimolar mount of the alcohol in the presence of a condensing agent such as dicyclohexylcarbodiimide or N-(3-dimethylaminopropyl)-N'-ethylcarbodiimide in a polar solvent such as methylene chloride, in the presence of a base if required, e.g. such as 4-(dimethylamino)pyridine.

Conversely, carboxylic acid esters can be convened to compounds of the invention with a free carboxy group using methods and conditions generally known in the an and illustrated herein. Depending on type of ester involved, useful reagents include aqueous acids or bases; also anhydrous reagents such as trialkylsilyl halides, hydrobromic acid in glacial acetic acid; also hydrogen and a hydrogenolysis catalyst For instance. trialkyl esters can be convened to the free trifunctional acids by treatment with hydrobromic acid in glacial acetic acid, e.g. at room temperature or elevated temperature. Also trialkyl esters can be convened to the mono esters wherein carboxy only remains esterified, by treatment with e.g. trimethylsilyl bromide at room temperature.

Any benzyl esters can be selectively hydrogenolyzed with e.g. hydrogen in the presence of a catalyst such as palladium on charcoal.

In the case mixtures of stereoisomers or optical isomers of the above compounds are obtained, these can be separated into the single isomers by methods in themselves known, e.g., by fractional distillation, crystallization and/or chromatography. Racemic products can be resolved into the optical antipodes, for example, by separation of diastereomeric salts thereof, e.g., for basic compounds by the fractional crystallization of d- or l-(tartrate, mandelate or camphorsulfonate) salts, or for acidic compounds by fractional crystallization of d- or l-(alpha-methylbenzylamine, cinchonidine, cinchonine, quinine, quinidine, ephedrine, dehydroabietylamine, brucine or strychnine)-salts.

The above-mentioned reactions are carried out according to standard methods, in the presence or absence of diluents, preferably such as are inert to the reagents and are solvents thereof, of catalysts, alkaline or acidic condensing or said other agents respectively and/or inert atmospheres, at low temperatures, room temperature or elevated temperatures, preferably near the boiling point of the solvents used, at atmospheric or superatmospheric pressure.

The invention further includes any variant of said processes, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being preferred.

The present invention additionally relates to the use in mammals of the compounds of the invention and their pharmaceutically acceptable, non-toxic acid addition salts, or pharmaceutical compositions thereof, as medicaments, e.g. as neutral endopeptidase inhibitors, e.g. for the treatment of cardiovascular disorders such as hypertension, edema, salt retention and congestive heart failure.

The present invention also relates to the use of the compounds of the invention for the preparation of pharmaceutical compositions especially pharmaceutical compositions having neutral endopeptidase inhibiting activity, and e.g. antihypertensive or saluretic activity.

The pharmaceutical compositions according to the invention are those suitable for enteral, such as oral or rectal, transdermal and parenteral administration to mammals, including man, for the treatment of cardiovascular disorders, such as hypertension, comprising an effective amount of a pharmacologically active compound of the invention or a pharmaceutically acceptable salt thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salts and/or polyethyleneglycol; for tablets also c) binders, e.g. magnesium aluminum silicate, starch paste, gelatin, tragacanth, methylcellulose, sodium carboxymethylcellulose and/or polyvinylpyrrolidone; if desired) disintegrants, e.g. starches, agar, alginic acid or its sodium salt, or effervescent mixes; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective mount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

A unit dosage for a mammal of about 50 to 70 kg may contain between about 10 and 100 mg of the active ingredient. The dosage of active compound is dependent on the species of warm-blooded animal (mammal), the body weight, age and individual condition, and on the form of administration.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. Optical rotations are measured at room temperature at 589 nm (D line of sodium), 365 nm or other wavelengths as specified in the examples.

The prefixes R and S are used to indicate the absolute configuration at each asymmetric center.

EXAMPLE 1

To a solution of N-(3-carbo(t)butoxy-1-oxopropyl)-(4S)-(p-phenylphenylmethyl)-4-amino-2R-methyl-butanoic acid ethyl ester (0.80 g) in 15 ml of $CH_2Cl_2$ at room temperature are added 3 ml of trifluoroacetic acid. The mixture is stirred overnight and concentrated. The residue is dissolved in tetrahydrofuran (THF), and 6.5 ml of 1N NaOH is added. The mixture is concentrated and triturated with ether. The solid can be recrystallized from methylene chloride-hexane to give sodium N-(3-carboxy-1-oxopropyl)-4S)-(p-phenylphenylmethyl)-4-amino-2R-methyl butanoic acid ethyl ester melting at 159°–160° C.; $[\alpha]_D^{20} = -11.4°$ (methanol).

The starting material is prepared as follows:

A solution of α-t-BOC-(R)-tyrosine methyl ester (5.9 g, 20 mmol) and pyridine (8 mL, 100 mmol) in methylene chloride (30 mL) is cooled to 0°–5° C. Trifluoromethanesulfonic anhydride (4 mL, 23 mmol) is added at 0°–5° C., and the resulting mixture is held for another 30 minutes. The reaction mixture is diluted with water (60 mL) and methylene chloride (100 mL), and washed sequentially with 0.5N sodium hydroxide solution (1×50 mL), water (1×60 mL), 10% citric acid solution (2×75 mL) and water (1×60 mL). The organic phase is dried over $MgSO_4$ and concentrated to an oil. The oil is purified by column chromatography (silica gel, hexane/ethyl acetate, 2:1 to give methyl(R)-2-(t-butoxycarbonylamino)-3-[4-(trifluoromethylsulfonyloxy)phenyl]-propionate which crystallizes on standing; m.p. 46°–48° C.; $[\alpha]^{20}_D - 36.01°$ (c=1,$CHCl_3$).

Nitrogen is passed through a suspension of (R)-2-(t-butoxycarbonyl-amino)-3-[4-(trifluoromethylsulfonyloxy)-phenyl]-propionate (1.75mmol), phenylboronic acid (3.5 mmol), anhydrous potassium carbonate (2.63 mmol) and toluene (17 mL) for 15 minutes. Tetrakis(triphenylphosphine)palladium(0) is added, and the mixture is heated at 85°–90° for 3 hours. The reaction mixture is cooled to 25° C., diluted with ethyl acetate (17 mL) and washed sequentially with saturated sodium bicarbonate (1×20 mL), water (1×20 mL), 10% citric acid (1×20 mL), water (1×20 mL) and saturated sodium chloride solution (1×20 mL). The organic phase is concentrated, and the residue is purified by column chromatography (silica gel, hexane/ethyl acetate 2:1) to yield methyl (R)-2-(t-butoxycarbonylamino)-3-(p-phenylphenyl)-propionate which can also be called N-(R)-t-butoxycarbonyl-(p-phenylphenyl)-alanine methyl ester.

To a solution of N-(R)-t-butoxycarbonyl-(p-phenylphenyl)-alanine methyl ester (6.8 g) in 60 ml of THF and 20 ml of methanol are added 20 ml of aqueous 1N sodium hydroxide solution. The mixture is stirred for 1 h at room temperature and then acidified with 21 ml of 1N hydrochloric acid. The aqueous solution is extracted 3x with ethyl acetate. The combined organic extracts are dried ($MgSO_4$), filtered and concentrated to give N-(R)-t-butoxycarbonyl-(p-phenylphenyl)-alanine, m.p. 98°–99° C., $[\alpha]^{20}_D - 18.59°$ (c=1, methanol).

To a solution of N-(R)-t-butoxycarbonyl-(p-phenylphenyl)-alanine (4.8 g) in 70 ml of methylene chloride ($CH_2Cl_2$) at 0° C. with 1.65 g of N,O-dimethylhydroxylamine HCl, 1.7 g of triethylamine and 2.85 g of hydroxybenzotriazole are added 5.37 g of 1-[3-(dimethylamino)propyl]-3-ethylcarbodiimide hycrochloride. The mixture is stirred 17 h at room temperature. The mixture is concentrated taken up in ethyl acetate (EtOAc) and washed with saturated sodium bicarbonate, 1N HCl and brine, then dried ($MgSO_4$), filtered and concentrated to give N-(R)-t-butoxycarbonyl-(p-phenylphenyl)-alanine N,O-dimethyl hydroxylamine aide.

To a 0° C. solution of N-(R)-t-butoxycarbonyl-(p-phenylphenyl)-alanine N,O-dimethyl hydroxylamine amide (5.2 g) in 250 ml of diethyl ether are added 0.64 g of lithium aluminum hydride. The reaction is stirred for 30 min. and quenched with aqueous potassium hydrogen sulfate. The mixture is stirred for additional 5 min., poured onto 1N HCl, extracted (3x) with EtOAc, dried ($MgSO_4$), filtered, and concentrated to give N-(R)4-t-butoxycarbonyl-(p-phenylphenyl)-alanine carboxaldehyde as a colorless oil.

To a 0° C. solution of N-(R)-t-butoxycarbonyl-(p-phenylphenyl)-alanine carboxaldehyde (4.4 g) in 200 ml of $CH_2Cl_2$ are added 10 g of carboethoxyethylidene phenyl phosphorane. The mixture is warmed to room temperature stirred for 1 h, washed with brine, dried ($MgSO_4$), filtered and concentrated. The residue is chromatographed on silica gel eluting with (1:2) ether:hexane to give N-t-butoxycarbonyl-(4R)-(p-phenylphenylmethyl)-4-amino-2-methyl-2-butenoic acid ethyl ester.

A solution of N-t-butoxycarbonyl-(4R)-(p-phenylphenylmethyl)-4-amino-2-methyl-2-butenoic acid ethyl ester (4.2 g) in 400 ml of ethanol is suspended with 2.0 g of 5% palladium on charcoal and then is hydrogenated at 50 psi for 6h. The catalyst is removed by filtration and the filtrate is concentrated to give N-t-butoxycarbonyl(4S)-(p-phenylphenylmethyl)-4-amino-2-methylbutanoic acid ethyl ester as a 80:20 mixture of diastereomers.

To the N-t-butoxycarbonyl(4S)-(p-phenylphenylmethyl)-4-amino-2-methylbutanoic acid ethyl ester (4.2 g) in 40 ml of $CH_2Cl_2$ at 0° C. is bubbled dry hydrogen chloride gas for 15 min. The mixture is stirred 2 h and concentrated to give (4S)-(p-phenylphenylmethyl)-4-amino-2-methylbutanoic acid ethyl ester hydrochloride as a 80:20 mixture of diastereomers.

To a room temperature solution of the above amine salt (3.12 g) in 15 ml of $CH_2Cl_2$ and 15 ml of pyridine are added 13.5 g of succinic anhydride. The mixture is stirred for 17 h, concentrated, dissolved in ethyl acetate, washed with 1N HCl and brine, and dried ($MgSO_4$) to give N-(3-carboxy-1-oxopropyl)-(4S)-(p-phenylphenylmethyl)-4-amino-2-methylbutanoic acid ethyl ester as a 80:20 mixture of diastereomers.

The above N-(3-carboxy-1-oxopropyl)-(4S )-(p-phenylphenylmethyl)-4-amino-2-methylbutanoic acid ethyl ester diastereomeric mixture (3.9 g) and N,N-dimethylformamide-di-t-butyl acetal (8.8 ml) are heated at 80° C. in 40 ml of toluene for 2 h. The mixture is poured onto ice-1N HCl, extracted with ether, chromatographed on silica gel eluting with (2:1) toluene:ethyl acetate to give N-(3-carbo(t)butoxy-1-oxopropyl)-(4S)-(p-phenylphenylmethyl)-4-amino-2R-methylbutanoic acid ethyl ester as the more polar material and the corresponding (S,S) diastereomer as the less polar material.

EXAMPLE 2

To a solution of N-(3-carboxy-1-oxopropyl)-(4S)-p-phenylphenylmethyl4-amino-(2R)-methylbutanoic acid ethyl ester (0.33 g) in 20 ml of (1:1)ethanol:tetrahydrofuran (THF) at room temperature are added 5 ml of 1N sodium hydroxide solution (NaOH) and stirred for 17 h. The mixture is concentrated, dissolved in water and washed with ether. The aqueous layer is acidified with 1N hydrochloric acid (HCl), extracted 3x with ethyl acetate (EtOAc), dried over magnesium sulfate (MgSO4), filtered and concentrated. The residue is triturated with ether to yield N-(3-carboxy-1-oxopropyl)-(4S)-p-phenylphenylmethyl-4-amino-(2R)-methylbutanoic acid melting at 158°–164° C., $[\alpha]_D^{20} = -23.5°$ (methanol).

EXAMPLE 3

Following the procedures described in Examples 1 or 2, the following compounds are prepared:

N-(3-carboxy-1-oxopropyl)-(4S)-(p-phenylphenylmethyl)-4-amino-2S-methylbutanoic acid melting at 165°–167° C.;

N-(3-carboxy-1-oxopropyl)-(4S)-[p-(4-methylphenyl)phenylmethyl]-4-amino-2R-methyl butanoic acid melting at 165°–170° C., $[\alpha]_D^{20} = -18.4°$ (c=1, methanol);

N-(3-carboxy-1-oxypropyl)-(4R)-p-phenylphenylmethyl-4-amino-2S-methylbutanoic acid, melting at 145°–149° C.;

N-(3-carboxy-1-oxopropyl)-(4R)-p-phenylphenylmethyl-4-amino-(2R)-methylbutanoic acid, melting at 162°–165° C.;

N-(3-carboxy-1-oxopropyl)-4(S,R)-p-phenylphenylmethyl-4-amino-2(S,R)-methyl butanoic acid, melting at 165°–167° C.;

Sodium N-(3-carboxy-1-oxopropyl)-4(S,R)-p-phenylphenylmethyl-4-amino-2(S,R)-methylbutanoic acid ethyl ester, melting at 165°–167° C.;

Sodium N-(3-carboxy-1-oxopropyl)-(4R)-p-phenylphenylmethyl-4-amino-2S-methylbutanoic acid ethyl ester, melting at 117°–120° C.;

N-(3-ethoxycarbonyl-1-oxopropyl)-(4S)-(p-phenylphenylmethyl)-4-amino-2R-methylbutanoic acid, melting at 178°–190° C.;

N-(2-carboxy-1-oxoethyl)-(4S)-p-phenylphenylmethyl-4-amino-2(S,R)-methylbutanoic acid, melting at 160°–161° C.;

N-(5-carboxy-1-oxopentyl)-(4S)-p-phenylphenylmethyl-4-amino-2R-methylbutanoic acid, melting at 124°–127° C.;

Sodium N-(3-carboxy-1-oxopropyl)-4(S,R)-p-phenylphenylmethyl-4-amino-2(S,R)-methoxybutanoic acid, melting at 180°–185° C.;

Sodium N-(3-carboxy-1-oxopropyl)-4(S,R)-p-phenylphenylmethyl-4-amino-2(S,R)-methoxybutanoic acid indanyl ester, melting at 134°–136° C.;

N-(3-carboxy-1-oxopropyl)-(4S)-p-phenylphenylmethyl-4-amino-butanoic acid, melting at 163°–166° C.;

N-(3-carboxy-3-hydroxy-1-oxopropyl)-(4S)-p-phenylphenylmethyl-4-amino-2R-methylbutanoic acid, melting at 156°–170° C.

EXAMPLE 4

Following the procedures described in example 1 except substituting glutaric anhydride for succinic anhydride, the following compounds are prepared:

N-(4-carboxy-1-oxobutyl)-(4S)-p-phenylphenylmethyl-4-amino- 2R-methylbutanoic acid, melting at 152°–155° C. Sodium N-(4-carboxy- 1 -oxobutyl)-(4S)-p-phenylphenylmethyl-4-amino-2R-methylbutanoic acid ethyl ester, melting at 68°–72° C.

EXAMPLE 5

Following the procedures described in example 1 except substituting carbobutoxyethylidene phenyl phosphorane for carboethoxyethylidene phenyl phosphorane, the following compound is prepared:

Sodium N-(3-carboxy-1-oxopropyl)-(4S)-p-phenylphenylmethyl-4-amino-2R-methylbutanoic acid n-butyl ester, melting at 155°–165° C.

EXAMPLE 6

To a room temperature solution of N-t-butoxycarbonyl-(4R)-p-phenylphenylmethyl-4-amino-2-methyl-2-butenoic acid ethyl ester (0.50 g) in 2 ml ethanol and 4 ml THF are added 2.0 ml of 1N NaOH. The reaction is stirred until the disappearance of starting material monitored by thin layer chromatography. The mixture is concentrated, dissolved in sodium bicarbonate and washed with ether. The aqueous layer is acidified with 3N HCl and extracted (3x) with ethyl acetate. The organic extracts are washed with brine, dried (MgSO4), filtered and concentrated to give N-t-butoxycarbonyl-(4R)-p-phenylphenylmethyl-4-amino-2-methyl-2-butenoic acid.

To a room temperature solution of N-t-butoxycarbonyl-(4R)-p-phenylphenylmethyl-4-amino-2-methyl -2-butenoic acid (0.30 g) in 10 ml of CH2Cl2 are added 0.123 g of dimethyl aminopyridine, 0.203 g of 5-indanol and 0.387 g of 1-[3-(dimethylamino)propyl]-3-ethylcarbodiimide hydrochloride. The mixture is stirred overnight, and then is concentrated and taken up in ethyl acetate. The organics are washed with saturated sodium bicarbonate (2x), 1N HCl (2x) and brine (2x), dried (MgSO4), filtered, concentrated and chromatographed on silica gel eluting with (1:4) ethyl acetate:hexane to give N-t-butoxycarbonyl-(4R)-p-phenylphenylmethyl-4-amino-2-methyl-2-butenoic acid indanyl ester. This material is convened to sodium N-(3-carboxy-1-oxopropyl)-(4S)-p-phenylphenylmethyl-4-amino-2R-methylbutanoic acid indanyl ester melting at 60°–65° C. according to the procedures described in example 1.

EXAMPLE 7

To a solution of (4S)-p-phenylphenylmethyl-4-amino-2-methylbutanoic acid ethyl ester hydrochloride (0.84 g) in 10 ml of methylene chloride are added 0.58 g d adipic acid mono methyl ester, 0.293 g of triethylamine, 0.49 g of hydroxybenzotriazole and 0.928 g of 1-[3-(dimethylamino)propyl]-3-ethylcarbodiimide hydrochloride. The reaction is stirred at room temperature overnight. The mixture is concentrated and the residue is taken up in ethyl acetate. The organics are washed with sodium bicarbonate, 1N HCl, brine, dried (MgSO4), filtered and evaporated. The residue is chromatographed on silica gel eluting with (1:2) ethyl acetate:hexane to give the more polar diastereomer N-(5-carbomethoxy-1-oxopentyl)-(4S)-p-phenylphenylmethyl-4-amino-2R-methylbutanoic acid ethyl ester. The less polar (S,S) diastereomer is also isolated.

To a solution of N-(5-carbomethoxy-1-oxopentyl)-(4S)-p-phenylphenylmethyl-4-amino-2R-methylbutanoic acid ethyl ester (0.58 g) in 10 ml of THF and 10 ml of ethanol are added 4.0 ml or 1N NaOH. The reaction is stirred overnight. The mixture is concentrated taken up in water and washed with ether (2x). The aqueous layer is acidified with 2N HCl and extracted with ethyl acetate (2x). The organics am dried (MgSO4), filtered, concentrated and recrystallized from methylene chloride-ether to give N-(5-carboxy-1-oxopentyl)-(4S)-p-phenylphenylmethyl-4-amino-2R-methylbutanoic acid, melting at 124°–127° C.

EXAMPLE 8

Preparation of 1,000 capsules each containing 50 mg of the active ingredient, as follows:

| | |
|---|---:|
| N-(3-carboxy-1-oxopropyl)-(4S)-(p-phenylphenyl-methyl)-4-amino-2R-methylbutanoic acid ethyl ester sodium salt | 50.00 g |
| Lactose | 187.00 g |
| Modified starch | 80.00 g |
| Magnesium stearate | 3.00 g |

Procedure: All the powders are passed through a screen with openings of 0.6 mm. The drug substance is placed in a suitable mixer and mixed first with the magnesium stearate, then with the lactose and starch until homogenous. No. 2 hard gelatin capsules am filled with 300 mg of said mixture each, using a capsule filling machine.

Analogously capsules are prepared, containing about 10–100 mg of the other compounds disclosed and exemplified herein, e.g. the compounds of examples 1–5.

What is claimed is:

1. A compound of formula I

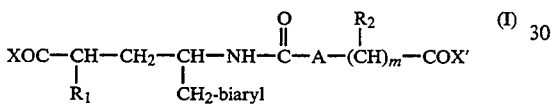

wherein COX and COX' independently represent carboxyl or carboxyl derivatized in form of a pharmaceutically acceptable ester or amide; $R_1$ represents hydrogen, lower alkyl, $C_3$–$C_7$-cycloalkyl-lower alkyl, aryl-lower alkyl, biaryl-lower alkyl, lower alkoxy, aryl-lower alkoxy, aryloxy, N-lower alkylamino, N,N-di-lower alkylamino, N-aryl-lower alkylamino, N,N-di-aryl-lower alkylamino, N-arylamino, N-N-diarylamino, lower alkanoylamino, aryl-lower alkanoylamino or aroylamino; $R_2$ represents hydrogen, hydroxy, lower alkoxy, lower alkyl, aryl-lower alkyl, $C_3$–$C_7$-cycloalkyl-lower alkyl, amino-lower alkyl, hydroxy-lower alkyl, lower alkylthio-lower alkyl, lower alkoxy-lower alkyl, aryl-lower alkylthio-lower alkyl or aryl-lower alkoxy-lower alkyl; biaryl represents phenyl substituted by carbocyclic or heterocyclic aryl; A represents a direct bond, lower alkylene, phenylene or cyclohexylene; m represents 1 or zero, provided that m represents 1 when A is a direct bond; carbocyclic aryl within the above definitions represents phenyl optionally substituted by lower alkyl, lower alkoxy, halogen, hydroxy, cyano, lower alkanoyloxy or trifluoromethyl; heterocyclic aryl represents thienyl or furanyl optionally substituted by lower alkyl; or a pharmaceutically acceptable salt thereof.

2. A compound according to claim 1 of formula Ia

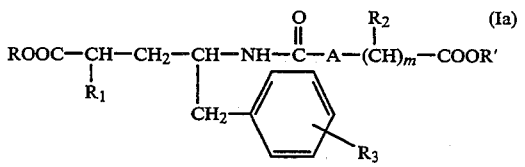

wherein COOR and COOR' independently represent carboxyl or carboxyl derivatized in form of a pharmaceutically acceptable ester, $R_1$ represents hydrogen, lower alkyl, lower alkoxy, N-lower alkylamino, lower alkanoylamino, aryl-lower alkyl, aryl-lower alkoxy, aryloxy, N-arylamino or aroylamino wherein aryl in each case represents phenyl optionally substituted by lower alkyl, lower alkoxy, halogen, hydroxy, cyano, acyloxy or trifluoromethyl; or aryl represents thienyl or furanyl optionally substituted by lower alkyl; $R_2$ represents hydrogen, hydroxy, lower alkyl or aryl-lower alkyl wherein aryl has the meaning given above, $R_3$ represents phenyl, or phenyl substituted by lower alkyl, lower alkoxy, halogen, cyano, lower alkanoyloxy or trifluoromethyl; or $R_3$ represents thienyl or furanyl optionally substituted by lower alkyl; A represents a direct bond, lower alkylene., 1,4-phenylene or 1,4-cyclohexylene; m represents 1 or zero provided that m represents 1 when A is a direct bond; or a pharmaceutically acceptable salt thereof.

3. A compound according to claim 2 wherein $R_3$ is located in the para position.

4. A compound according to claim 1 of formula Ib

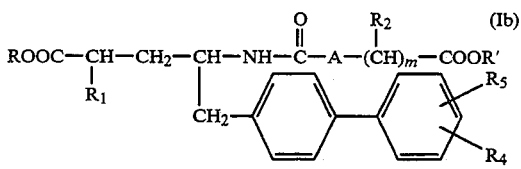

wherein COOR and COOR' independently represent carboxyl or carboxyl derivatized in form of a pharmaceutically acceptable ester, $R_1$ is hydrogen, lower alkyl, lower alkoxy or aryl-lower alkyl wherein aryl represents phenyl optionally substituted by lower alkyl, lower alkoxy, halogen, hydroxy, cyano, acyloxy or trifluoromethyl; $R_2$ represents hydrogen, hydroxy or lower alkoxy; $R_4$ and $R_5$ independently represent hydrogen, lower alkyl, hydroxy, lower alkoxy, halogen, cyano or trifluoromethyl; A represents lower alkylene; m represents 1 or zero; or a pharmaceutical acceptable salt thereof.

5. A compound according to claim 4 of formula Ic

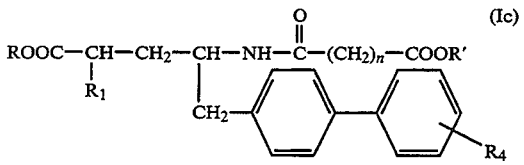

wherein COOR and COOR' independently represent carboxyl or carboxyl derivatized in form of a pharmaceutically acceptable ester, $R_1$ is lower alkyl or lower alkoxy; $R_4$ represents hydrogen, lower alkyl, lower alkoxy, halogen, or trifluoromethyl; n represents an integer 1 through 6; or a pharmaceutical acceptable salt thereof.

6. A compound according to claim 5 of formula Ic wherein COOR and COOR' independently represent carboxyl, $C_1$–$C_{20}$-alkoxycarbonyl, (carbocyclic or heterocyclic aryl)-lower alkoxycarbonyl, (di-lower alkylamino, N-lower alkylpiperazino, morpholino, pyrrolidino, piperidino or perhydrazepino)-$C_2$ to $C_4$-alkoxycarbonyl,dihydroxypropyloxycarbonyl protected in form of a ketal, 5-indanyloxycarbonyl, 3-phthalidoxycarbonyl, bicycloalkoxycarbonyl-lower alkoxycarbonyl, α-(lower alkoxycarbonyl or di-lower alkylaminocarbonyl)-lower alkoxycarbonyl, 1-(lower alkoxycarbonyloxy)-lower alkoxycarbonyl or 1-(lower alkanoyloxy)-lower alkoxycarbonyl; or a pharmaceutically acceptable salt thereof.

7. A compound according to claim 1 of formula Id

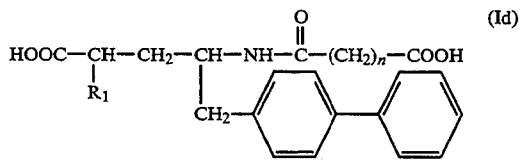

wherein R₁ is lower alkyl; n is an integer 1 through 4; or a pharmaceutically acceptable mono- or di-ester derivative thereof in which one or two of the acidic hydroxy groups of the carboxyl functional groups are esterified in form of a mono- or di-pharmaceutically acceptable ester, or a pharmaceutically acceptable salt thereof; or an optical antipode thereof.

8. A neutral endopeptidase inhibiting pharmaceutical composition comprising an effective neutral endopeptidase inhibiting amount of a compound of claim 1 in combination with one or more pharmaceutically acceptable carriers.

9. A method of treating cardiovascular disorders which comprises administering to a mammal in need of such treatment an effective neutral endopeptidase inhibiting amount of a compound of claim 1 in combination with one or more pharmaceutically acceptable carriers.

10. A compound according to claim 5 being N-(3-carboxy-1-oxopropyl)-4-(p-phenylphenylmethyl)-4-amino-2-methoxybutanoic acid or a pharmaceutically acceptable salt thereof.

* * * * *